US00PP28292P3

(12) United States Plant Patent
Van Dijk

(10) Patent No.: US PP28,292 P3
(45) Date of Patent: Aug. 15, 2017

(54) ***ANTHURIUM* PLANT NAMED 'ANTHDOTXI'**

(50) Latin Name: ***Anthurium andreanum* L.**
Varietal Denomination: ANTHDOTXI

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 91 days.

(21) Appl. No.: 14/757,197

(22) Filed: Dec. 3, 2015

(65) Prior Publication Data

US 2017/0164541 P1 Jun. 8, 2017

(51) Int. Cl.
*A01H 5/02* (2006.01)

(52) U.S. Cl.
USPC ..... Plt./369

(58) Field of Classification Search
USPC ..... Plt./369
See application file for complete search history.

(56) References Cited

PUBLICATIONS

UPOV hit on *anthurium* plant named 'Anthdotxi', European Union, Jul. 5, 2013.*

* cited by examiner

*Primary Examiner* — Anne Grunberg
(74) *Attorney, Agent, or Firm* — Jondle & Associates, P.C.

(57) ABSTRACT

A new and distinct variety of *Anthurium* plant named 'ANTHDOTXI' particularly distinguished by having large bright red, heart-shaped and very durable spathes that retain the original color for a very long period of time, dark green and cordate, durable leaves, red cataphylls, rich flowering continuously throughout the year and a plant height of 50 cm to 55 cm, is disclosed.

3 Drawing Sheets

Genus and species: *Anthurium andreanum* L.
Variety denomination: 'ANTHDOTXI'.

BACKGROUND OF THE NEW PLANT

The present invention comprises a new and distinct variety of *Anthurium*, botanically known as *Anthurium andreanum* L., and hereinafter referred to by the variety name 'ANTHDOTXI'. The new variety originated from a hybridization made in June 2006 in Bleiswijk, The Netherlands. The female parent was a red *Anthurium* pot plant designated '9632-01' (unpatented), and the male parent was a red *Anthurium* plant designated '9863-01' (unpatented).

A single plant was selected in June 2008 and has been asexually reproduced repeatedly by tissue culture in Bleiswijk, The Netherlands over a seven-year period. The present invention has been found to retain its distinctive characteristics through successive asexual propagations.

Plant Breeder's Rights for this variety have been applied for in the European Union on Jul. 5, 2013 and in Vietnam on Apr. 10, 2015. 'ANTHDOTXI' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Large, bright red, cordate spathe;
2) White spadix with yellow tip;
3) Dark green, glossy, long cordate leaves; and
4) Red cataphyll.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 40-week old plant grown in a greenhouse in Bleiswijk, The Netherlands in July 2015.

DESCRIPTION OF THE NEW VARIETY

Figure 1:
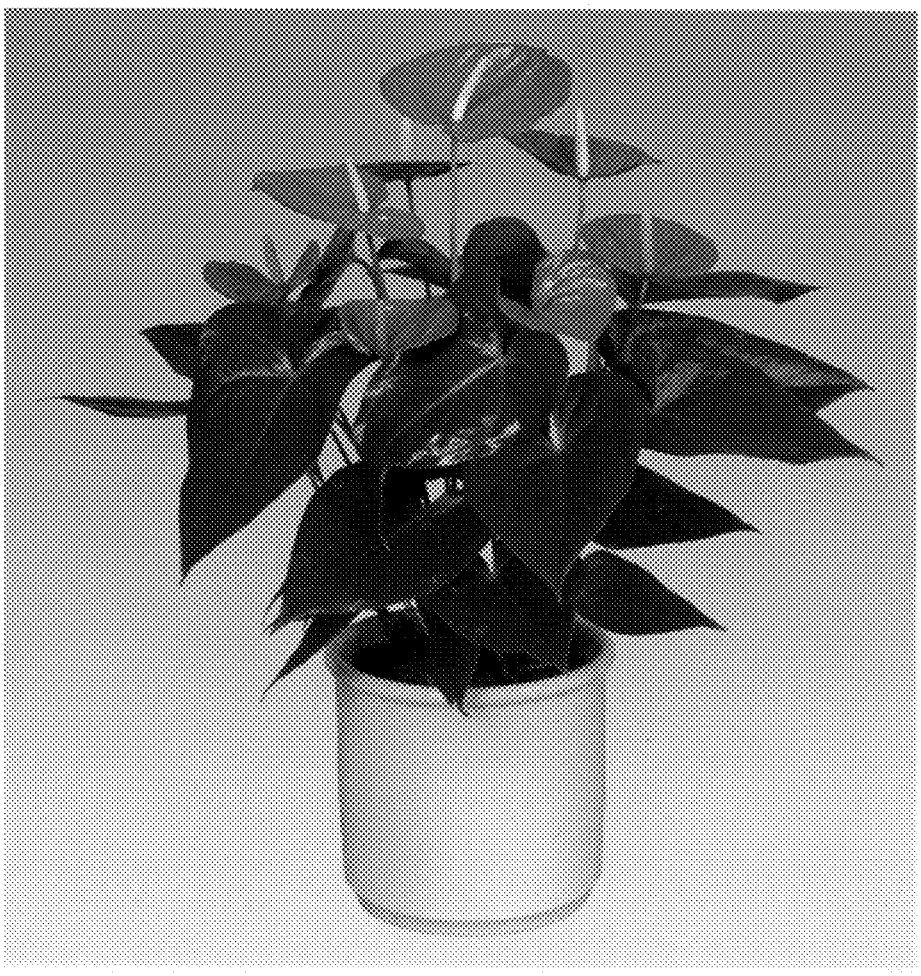
FIG. 1 shows the overall plant habit, including blooms and foliage.
Figure 2:
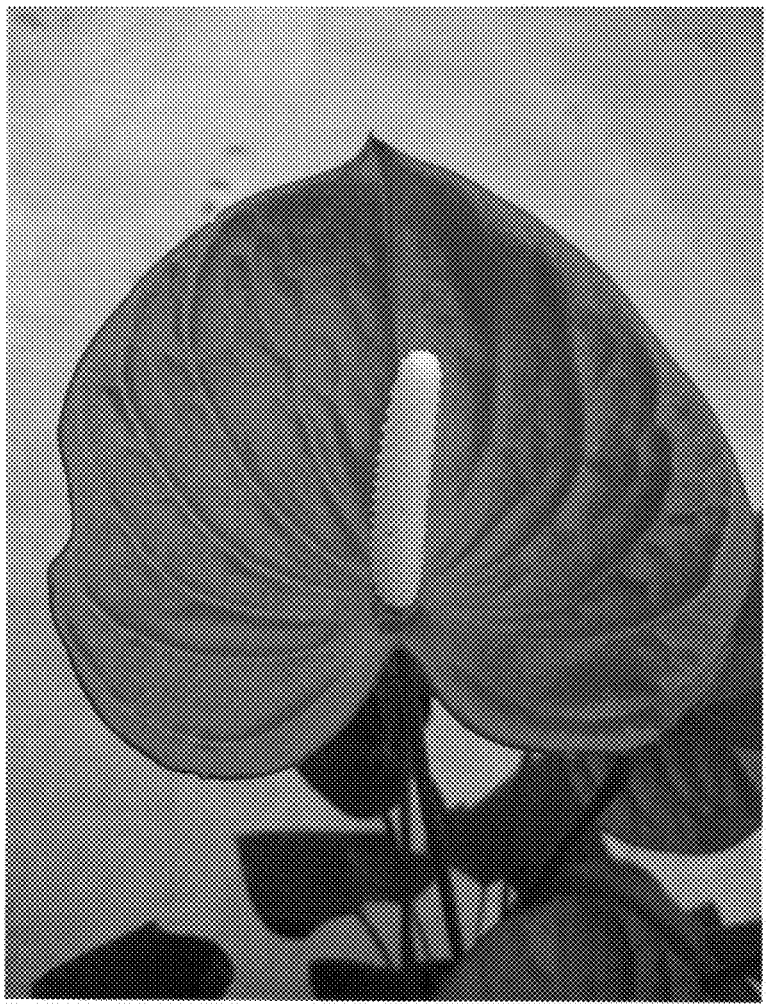
FIG. 2 shows a close-up of the mature spathe.
Figure 3:
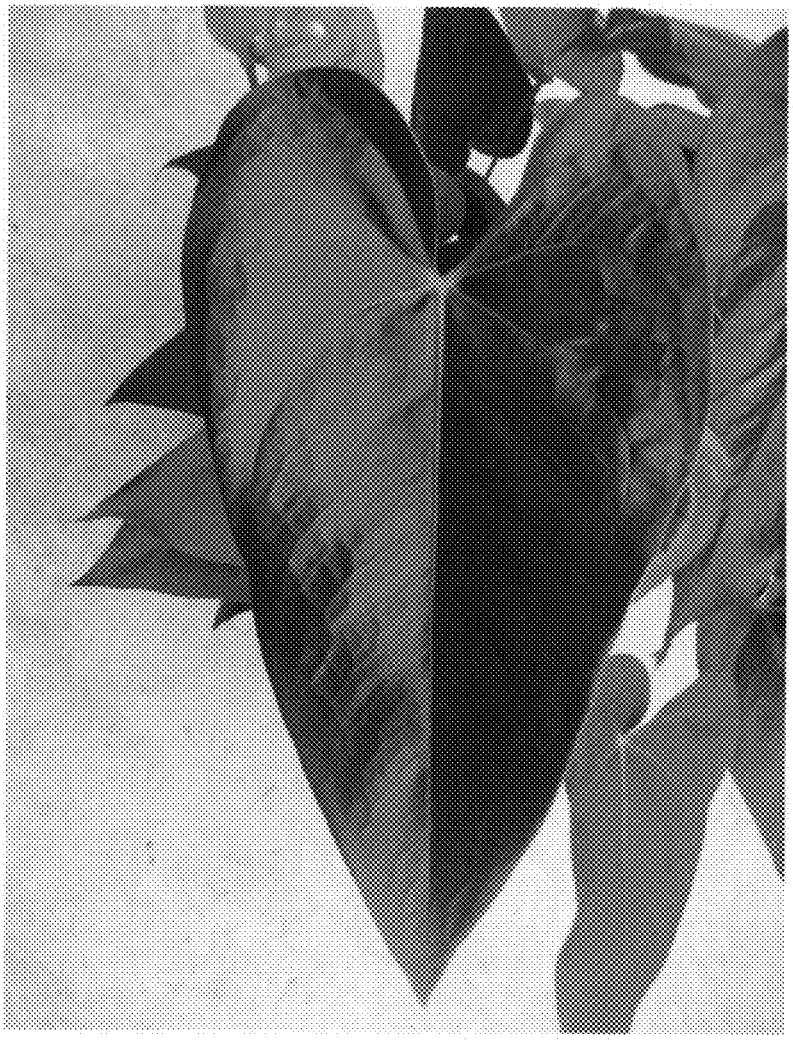
FIG. 3 shows the upper leaf blade surface.

The following detailed description sets forth the distinctive characteristics of 'ANTHDOTXI'. The data which define these characteristics were collected from asexual reproductions carried out in Bleiswijk, The Netherlands. The plant history was taken on 40-week old plants which were planted from tissue culture in 17-centimeter pots and grown in a glass greenhouse between 19° C. and 24° C. Observations were made in July 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHDOTXI'.

Parentage:

*Female parent*.—*Anthurium* plant '9632-01' (unpatented).

*Male parent*.—*Anthurium* plant '9863-01' (unpatented).

Plant:

*Propagation*.—Tissue culture.

*Root description*.—Fleshy-white colored roots with small hairy lateral roots having yellow-colored root tips.

*Time to produce a finished flowering plant*.—35 to 40 weeks for a 17 cm pot.

*Growth habit*.—Herbaceous perennial.

*Height* (*measured from soil, including inflorescence*).—50.0 cm to 55.0 cm.

*Width* (*measured from leaf tips*).—45.0 cm to 50.0 cm.

Leaves:

*Immature leaves*.—Length: 20.0 cm to 25.0 cm. Width: 10.0 cm to 15.0 cm. Color: Upper surface: RHS 146A. Lower surface: RHS 146B. Texture (both upper and lower surfaces): Shiny.

*Mature leaves*.—Length (fully expanded): 20.0 cm to 25.0 cm. Width: 10.0 cm to 15.0 cm. Shape: Deltoid. Apex: Acute. Base: Cordate. Leaf blade angle with the petiole: Between 100 degrees and 120 degrees. Leaf margin: Entire. Color: Upper surface: RHS 147A. Lower surface: RHS 147B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C.

*Lobes*.—Arrangement: Leaf blade has two lobes extending past the petiole. The lobes are non-touching. Length of lobes of mature leaf blades: 2.0 cm to 6.0 cm. Width of lobes of mature leaf blades: 5.0 cm to 7.0 cm. Distance for petiole/leaf junction to highest point on lobes of mature leaf blades: 2.0 cm to 4.0 cm.

*Petiole*.—Cross-section: Round. Diameter: 0.2 cm to 0.3 cm. Length: 20.0 cm to 30.0 cm for a mature leaf size. Color: Mature leaf: RHS 144B. Immature leaf: RHS 144B. Cataphyll color surrounding the petiole: Outside: RHS 48A. Inside: RHS 48B.

*Geniculum*.—Length: 2.5 cm to 3.0 cm. Width: 0.3 cm to 0.4 cm. Color: RHS 144A.

Inflorescence:

*Arrangement*.—Single.

*Flowering habit* (*length of flowering season*).—Continuous.

*Number of inflorescences per plant*.—5 to 7.

*Fragrance*.—Absent.

*Longevity of inflorescence on plant*.—Over a year.

*Longevity of inflorescence when cut*.—45 to 55 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 100 degrees and 120 degrees; the spathe stands on a wiry peduncle about 3.0 cm to 5.0 cm above the foliage.

*Shape*.—Cordate.

*Apex*.—Mucronate.

*Base*.—Cordate.

*Texture*.—Shiny and slightly blistered.

*Margin*.—Entire.

*Size*.—Length: 9.0 cm to 13.0 cm. Width: 9.0 cm to 14.0 cm.

*Lobes*.—Arrangement: The spathe has two lobes extending past the peduncle. The lobes are non-touching. Length: 2.0 cm to 3.0 cm. Width: 4.0 cm to 7.0 cm.

*Color*.—Just fully open: Upper surface: RHS 45A. Lower surface: RHS 45B. This red color remains for a very long period, at least more than 30 weeks after opening.

Peduncle:

*Shape*.—Erect.

*Cross-section*.—Round.

*Length*.—25.0 cm to 45.0 cm.

*Diameter*.—0.2 cm to 0.3 cm.

*Color*.—RHS 144B.

Flowering time:

*General*.—One small rooted untreated tissue culture plant of 8.0 cm tall will flower after 8 to 9 months, depending on the season, and 4 to 6 blossoms appear. More blossoms appear after some additional weeks so that a full flowering and commercial plant will have 6 to 8 red spathes. Smaller blossoms may occur on less mature plants.

Spadix:

*Size*.—Length: 3.0 cm to 5.0 cm (depending on flower size). Width (at apex): 0.4 cm to 0.5 cm. Width (at base): 0.7 cm to 0.8 cm.

*Shape*.—Columnar.

*Angle from spadix tip to peduncle*.—160 to 180 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 15A. Mature: RHS 158C. Aged: RHS 144A.

Flowers:

*Quantity per spadix*.—240 to 280.

*Spadix flower arrangement*.—Bisexual, rounded in cross-section.

*Shape*.—Rounded.

*Size*.—Length: 0.05 cm to 0.1 cm. Diameter (maximum): 0.1 cm Color: RHS 158C.

Reproductive organs:

*Stamens*.—Not visible.

*Pollen amount*.—Very few.

*Pollen color*.—RHS 156D.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed.

COMPARISON WITH PARENTAL AND COMMERCIAL VARIETIES

'ANTHDOTXI' differs from the female parent plant '9632-01' (unpatented) in that 'ANTHDOTXI' has a larger spathe width than '9632-01'.

'ANTHDOTXI' differs from male parent plant '9863-01' (unpatented) in that 'ANTHDOTXI' has a geniculum that is lighter green than the petiole, whereas '9863-01' has a geniculum that is darker green than the petiole.

'ANTHDOTXI' differs from commercial variety 'ANTHBNZL' (U.S. Plant Pat. No. 17,134) in that 'ANTHDOTXI' has a yellow immature spadix and a red cataphyll, whereas 'ANTHBNZL' has an orange-yellow immature spadix and a green cataphyll. Additionally, 'ANTHDOTXI' has a more round spathe shape, whereas 'ANTHBNZL' has a more elliptical spathe shape.

'ANTHDOTXI' differs from commercial variety 'ANTHCITOK' (unpatented) in that 'ANTHDOTXI' has a red cataphyll, whereas 'ANTHCITOK' has a green cataphyll. Additionally, 'ANTHDOTXI' has shorter leaf lobes than 'ANTHCITOK' and a less red color in summer on the lower surface of the young spathe than that of 'ANTHCITOK'.

I claim:

1. A new and distinct variety of *Anthurium* plant named 'ANTHDOTXI', substantially as illustrated and described herein.

* * * * *